United States Patent
Walter et al.

(10) Patent No.: US 9,297,821 B2
(45) Date of Patent: Mar. 29, 2016

(54) METHOD FOR TESTING AN ANALYTICAL INSTRUMENT

(71) Applicant: Mettler-Toledo AG, Greifensee (CH)

(72) Inventors: Christian Walter, Herrliberg (CH); Félix Bécheiraz, Bülach (CH); Manuela Gerber, Winterthur (CH); Rolf Rohner, Volketswil (CH)

(73) Assignee: Mettler-Toledo GmbH, Greifensee (CH)

( * ) Notice: Subject to any disclaimer, the term of this patent is extended or adjusted under 35 U.S.C. 154(b) by 134 days.

(21) Appl. No.: 14/179,165

(22) Filed: Feb. 12, 2014

(65) Prior Publication Data

US 2014/0227791 A1    Aug. 14, 2014

(30) Foreign Application Priority Data

Feb. 14, 2013   (EP) ..................................... 13155158

(51) Int. Cl.

| | |
|---|---|
| *G01N 31/16* | (2006.01) |
| *G01N 1/10* | (2006.01) |
| *G01N 21/41* | (2006.01) |
| *G01N 35/00* | (2006.01) |
| *G01N 9/00* | (2006.01) |
| *G01J 3/02* | (2006.01) |
| *G01N 21/13* | (2006.01) |

(52) U.S. Cl.
CPC ......... *G01N 35/00732* (2013.01); *G01J 3/0267* (2013.01); *G01N 1/10* (2013.01); *G01N 9/00* (2013.01); *G01N 21/13* (2013.01); *G01N 21/41* (2013.01); *G01N 31/16* (2013.01); *G01N 35/00613* (2013.01); *G01N 35/00623* (2013.01); *G01N 2035/00683* (2013.01); *Y10T 436/10* (2015.01)

(58) Field of Classification Search
CPC ......... G01J 3/0267; G01N 1/10; G01N 35/00; G01N 35/00594; G01N 35/00613; G01N 35/00623; G01N 35/00732; G01N 2035/00683; G01N 9/00; G01N 21/13; G01N 21/41; G01N 31/16; Y10T 436/10; Y10T 436/11; Y10T 436/12
USPC ................... 436/8, 43, 51, 55, 163, 164, 166; 422/67, 68.1, 75, 82.05, 82.09; 73/1.01, 1.02, 32 R, 64.56; 356/51, 128
See application file for complete search history.

(56) References Cited

U.S. PATENT DOCUMENTS

| | | |
|---|---|---|
| 6,080,364 A | 6/2000 | Mimura et al. |
| 6,579,717 B1 | 6/2003 | Matsubara et al. |
| 8,313,695 B2 | 11/2012 | Akutsu |

(Continued)

*Primary Examiner* — Maureen Wallenhorst
(74) *Attorney, Agent, or Firm* — Standley Law Group LLP

(57) ABSTRACT

A method and system for testing the functional capability of an analytical instrument uses first and second blind samples. Each blind sample is a test substance with an amount of a parameter to be tested that is unknown to the user. Each blind sample is provided with an identification means with a unique identification. When the blind samples are tested by the user in the instrument being tested, the measurement values obtained and the unique identifications read are compared against predetermined values that are accessible to a test program configured as software on the analytical instrument. By comparison of the measurement values and the predetermined values, the functional capability of the analytical instrument is determined and the result is transmitted to an output unit of the analytical instrument.

16 Claims, 4 Drawing Sheets

(56) References Cited

U.S. PATENT DOCUMENTS

| | | |
|---|---|---|
| 2007/0217949 A1 | 9/2007 | Mimura et al. |
| 2008/0056944 A1 | 3/2008 | Nakamura et al. |
| 2008/0219887 A1 | 9/2008 | Akutsu |
| 2009/0198463 A1 | 8/2009 | Kamihara et al. |
| 2010/0145630 A1 | 6/2010 | Ball et al. |
| 2011/0090066 A1 | 4/2011 | Yamaguchi et al. |
| 2013/0011298 A1 | 1/2013 | Itou et al. |
| 2013/0039809 A1 | 2/2013 | Akutsu |

METHOD FOR TESTING AN ANALYTICAL INSTRUMENT

CROSS-REFERENCE TO RELATED APPLICATIONS

This application is entitled to benefit of a right of priority under 35 USC §119 from European patent application 13155158.2, filed on 14 Feb. 2013, the content of which is incorporated by reference as if fully recited herein.

TECHNICAL FIELD

The invention relates to a method for testing the functional capability of an analytical instrument using at least one blind sample, as well as a blind sample for carrying out this method.

BACKGROUND

Analytical instruments are used both in laboratories and in the production or process fields for chemical and/or physical analysis, such as in quantitative analysis, for example. Quantitative analysis is a chemical and/or physical procedure for determining the quantity or amount of a material or a substance in a sample to be analysed. An analytical instrument may be what is known as a bench-top instrument, hand-held instrument or in-line instrument. In addition, analytical instruments are also used in order to determine other chemical and/or physical properties or parameters of a sample.

Examples of analytical instruments of this type are titrators, UV/VIS spectrometers, refractometers and instruments for measuring density, for determining pH, for determining redox potentials, for conductivity determination, for ion determination and/or for the determination of dissolved gases. Using such instruments, various parameters of at least one substance in a sample can be determined, examples of which are the concentration, amount, density, refractive index, pH, redox potential and/or conductivity. Analytical instruments can be fitted out for determining one or more parameters of a sample.

The functional capability of analytical instruments should be regularly tested in order to ensure that the quality and reproducibility of the measurement results is consistent. Regular testing is generally carried out by the operator, who measures one or more known samples and compares the result with an expected set value. Samples which have contents and parameters or set values which are known to the operator are known as "known" samples. Samples in which the contents, parameters or set values are unknown to the operator, but are known to the person submitting them, are "blind" samples and are used to test the validity of a measurement instrument or an analytical instrument or of the process being conducted on the instrument. In addition, analytical instruments can be serviced on site by the manufacturer or a certificated service engineer; this is very expensive for the operator and thus is mainly only carried out in areas and/or applications for which appropriate independent certification is required.

In order to carry out the testing successfully, the operator should have a great deal of experience using the analytical instrument to be tested and above all be able to guarantee that the samples to be examined are of consistent quality. The chemical and/or physical analytical methods provided as examples are very precise and react to the slightest contamination of the sample due to foreign bodies and/or old samples with erroneous readings. Measuring a contaminated and/or old sample provides a measuring result which is correct for that sample, but which deviates substantially from the expected result for the known and preferably pure sample. Testing an analytical instrument by an operator can thus be fraught with errors, and in addition can be influenced by the operator who is aware of the physical and/or chemical processes which are occurring.

Thus, there is a need for a method for independent testing and/or validation of an analytical instrument which is simple and inexpensive for the operator to carry out, and for an analytical instrument for carrying out this method. The aim of the method is, inter alia, to reduce operator-derived errors, examples of which are errors in weighing out and/or dosing errors, so that even inexperienced operators can carry out a reliable and independent test of the analytical instrument.

SUMMARY

A method for testing an analytical instrument comprises the following steps: providing the analytical instrument, which comprises at least one sensor, a control unit and a test program; selecting the test program; providing at least a first and second blind sample, which each comprises a test substance and an identification means with an unique identification of the respective test substance; testing the instrument configuration of the analytical instrument; measuring the first blind sample with the analytical instrument and acquiring at least a first measurement value; measuring the second blind sample with the analytical instrument and acquiring at least a second measurement value; acquiring and transferring the first and second identification and the first and second measurement values to a test unit and, by means of the test unit: identifying the first and second test substance and a first and second set value for the first and second blind sample by means of the first and second identification, determining a test result by comparing the first and second measurement values and/or at least one test value determined using the first and/or second measurement values with the set values for the first and second blind sample having regard to a first and second threshold value, which has been stored in the test unit; providing an output unit and transferring the test result to the control unit and outputting the test result by means of the output unit.

By means of the method, an operator can measure at least two blind samples which are unknown to him and by means of the first and second measurement value determined for the respective blind sample can obtain a declaration of the functional capability of the analytical instrument. Each blind sample comprises an identification means with an unique code which is herein termed "identification". By means of the identification, each blind sample can be uniquely identified and both the test substance contained therein and also the set value for each blind sample can be determined. By means of a comparison between the first and second measurement value and the first and second set value in the light of the predetermined first and second threshold value, a test result can be determined which can act as a declaration of the functional capability of the analytical instrument using the output unit.

As an example, the output unit may be a display unit, for example a display or a monitor, a printer, a storage module and/or a means for optical and/or acoustic display. The result may, for example, be presented to the operator as an optical or acoustic signal, as a document, stored in the analytical instrument and/or archived as a certificate, either electronically and/or on paper.

The functional capability is tested using at least a first and a second blind sample, wherein the first blind sample comprises the first test substance and the first identification means with the first identification and the second blind sample comprises the second test substance and the second identification means with the second identification.

In this manner, an operator-independent test of the functional capability of the analytical instrument is made possible, since the operator does not know the actual values for the relevant parameters of the respective blind sample, herein termed "set value".

For the respective instrument and/or the method to be tested, the operator obtains first and second blind samples which can be measured directly without any further preparation. In this manner, errors in sample preparation, such as errors in weighing out or diluting the test substance, can be almost completely avoided and so the precision of the test is improved. In addition, errors in manipulating the measurement by the operator can be reduced, since if he knows the set value and the instrument to be tested, he could manipulate the measurements, for example by breaking off the measurement too soon, or moving the sample or the instrument in order to make the measurement value agree with the set value.

Testing the instrument configuration of the analytical instrument may include manual or direct testing using a questionnaire in the test program or, for example, a list in the manual or the instructions, or an essentially automated testing using the control unit. In addition, when testing the instrument configuration, the blind samples to be measured could be checked as to whether the selected instrument configuration is actually suitable for the blind samples employed. If this is not the case, then the operator could receive an error message along with the possibility of correcting the instrument configuration even before measurements of the blind sample are taken.

The test result is presented as an error message, a simple confirmation, an independent confirmation or as a validated confirmation of the functional capability of the analytical instrument.

An error message is shown when, on comparing the first and second measurement value with the first and second set value, the deviation from the predetermined first and second threshold value is shown to be too large. The allowed deviation of the first and second set value from the corresponding threshold value, along with the first and second threshold value, is preferably determined using the analytical instrument to be tested and/or the application, preferably from the instrument manufacturer. Too large a deviation may, for example, be an indication of an incorrect instrument configuration, of using wrong, old and/or contaminated reagents and also of a wrong or defective sensor. An example of a wrong sensor is a sensor that is unsuitable for the measurement. A sensor may be defective if it is wrongly calibrated, aligned, old and/or faulty. Depending on the analytical instrument and test program, an error message or an error analysis with an indication as to how to rectify the error may be presented to the operator.

A simple confirmation of the functional capability of the analytical instrument can be presented to the operator as the test result if at least two blind samples are measured. The two blind samples may be different or identical as regards the test substance therein and its parameters. A simple confirmation allows the operator to carry out a rapid test of the functional capability of the analytical instrument and can be carried out at times set by the operator. A simple confirmation can, for example, be in the form of a single symbol or signal given out by the output unit.

Correlation of a first and second measurement value can provide indications of the functional capability of an analytical instrument, however the validity of an evaluation based on two measurement values is limited. As discussed above, an evaluation based on two measurement values is suitable for a rapid test. An independent confirmation of the functional capability of the analytical instrument, which comprises the measurement of at least a first, second and third blind sample and the determination of at least a first, second and third measurement value is statistically more significant. An example of an independent confirmation presented to the operator is a document and/or display which is a manufacturer's confirmation or a certificate regarding the functional capability of the corresponding analytical instrument. This document may, for example, be printed out, filed and/or stored by the operator as a test certificate.

Furthermore, a validated confirmation of the functional capability of the analytical instrument can be output as the test result when, for example, the standard requirements for the respective analytical instrument or the application to be carried out have been complied with. A validated confirmation is preferably also based on the measurement of at least a first, second and third blind sample.

The unique identification of the identification means comprises a machine readable code, such as a serial number, a barcode, a matrix code and/or a RFID tag. In this manner, the identification of any blind sample can be read particularly easily and relayed to the test unit; the identification can be transferred both manually and automatically. A manual transfer is, for example, inputting a serial number by keying it in. Automatic transfer concerns reading off the identification with a suitable reader which transfers the identification directly to the control unit and/or test unit. The reader can preferably transfer the identification directly to the test and/or control unit. The reader may be integrated into the analytical instrument as a component, or it may be an external instrument.

The identification may contain the set value and/or other parameters of the test substance for the respective blind sample as encrypted values; the data required to decipher the information is stored in the test unit. Equally, these parameters could be stored in a database and be called from the database by the test unit via the respective identification.

The test unit may be a subunit of the control unit. This is advantageous when the parameters from the blind samples are also stored directly in the test unit or can be deciphered therefrom, and thus, for example, stand-alone instruments with no internet access or no interface to a higher level system can be tested directly.

The test unit may be an external unit which is independent of the analytical instrument. This external unit may, for example, be web-based software, a database on a processing unit which is independent of the operator, for example the manufacturer's, and/or a processing unit which is independent of the analytical instrument, such as a portable data processer which is for example used in instrument maintenance.

The test unit may comprise a database with which the identification of the first, second and/or further identification means is correlated with the corresponding set values and/or the corresponding test substances of each blind sample.

One embodiment of the method of the invention comprises an analytical instrument which is a titrator, which comprises a sensor, at least one dosing element, at least one titration solution with a known titre which is dispensed with the dosing element, and a control unit in which a test program is stored. The method for testing the titrator comprises the following steps: selecting the test program; providing a first and second blind sample in the form of a solution, wherein each blind sample comprises a test substance and an identification means with the unique identification of the respective test substance; testing the instrument configuration of the titrator; titrating the first blind sample against the at least one titration solution and acquiring a first measurement value and titrating the second blind sample against the at least one titration solution and acquiring a second measurement value, wherein the first and second measurement values are correlated with the consumption of titration solution for the respective titration; and acquiring and transferring the identifications of the first and second blind sample, the titre and the first and second measurement values to the test unit. By means of the test unit, the first and second test substance and the first and second set amount of the first and second test substance can be identified as the first and second set value by means of the respective identification, the first and second amount of the first and second test substance can be determined and a test result can be determined by comparison of the determined first and second amounts with the first and second set amounts having regard to the first and second threshold values stored in the test unit. The test result is transferred to the control unit and displayed by means of the output unit which is provided.

Applying the method of the invention to a titrator as the analytical instrument is of particular advantage. The blind samples are provided to the operator as ready-made solutions of a suitable test substance so that in particular weighing out and dilution errors, as well as errors brought about by contaminated and/or old test substances are minimized or may even be avoided. In addition, blind samples for a specific application or for a specific instrument configuration may be provided.

Titration is a quantitative method in chemistry for determining the amount or concentration of a substance in a solution. A test solution of a known material the concentration or amount of which is unknown is reacted in a specific chemical reaction with a titration solution which is specific for the test substance and which is of known concentration and/or titre. The term "titre" means the ratio of the actual concentration of a titration or bulk solution and the desired concentration of that same solution. Thus, the titre is a factor which characterizes normal solutions. The volume of the titration solution consumed during the titration is measured and the unknown concentration of the test solution is calculated from the stoichiometry of the reaction which has occurred. The equivalence point or end point of the titration can be determined visually using a suitable indicator by means of a colour change or by using a suitable sensor. Inter alia, acid-base titrations for determining a concentration of an acid or base, precipitation titrations, thermometric titrations, complexometric determinations and redox titrations, as well as Karl-Fischer titrations for determining water content, are known. Since the measurement results for optimized titration methods are very precise and titrations lend themselves well to being automated, titrations are widely used in analytical chemistry. An automated titration instrument is known as a titrator.

A further embodiment comprises carrying out the method of the invention for a UV/VIS spectrometer as the analytical instrument, which comprises a sensor, a radiation source and a control unit in which a test program is stored. The method thus comprises the following steps: selecting the test program; providing the first and second blind sample in the form of solutions, wherein each blind sample comprises a test substance and an identification means with the unique identification of the respective test substance; testing the instrument configuration of the spectrometer; determining at least a first and second absorption value and/or a first and second intensity of the first and second absorption value as the first and second measurement value; acquiring and transferring the identification and the first and second measurement value to the test unit and, by means of the test units; identifying the first and second test substance and a first and second set value for the respective blind sample by means of that identification; determining a first and second test value using the first and second measurement value, wherein the test value is the quantity and/or the test substance in the respective blind sample; determining the test result by comparing the first and second test value with the first and second set value making use of the first and second threshold values stored in the test unit; transferring the test result to the control unit and outputting the test result using the output unit provided.

Clearly, instead of an absorption value, a transmission value may also be acquired; these two values can be converted between themselves using a computation.

Carrying out the test method for a UV/VIS spectrometer is advantageous, since blind samples can be provided to the operator which are specific for particular applications and/or particular instrument configurations. In addition, weighing and dilution errors as well as errors due to contaminated or old test substances can be avoided or at least reduced. Testing of a UV/VIS spectrometer can comprise measuring two or more identical or different blind samples.

In contrast to titration, the blind sample is not consumed during UV/VIS spectroscopy and so it can be used a number of times. In order to prevent an old blind sample from being used by the operator, a "best-before" date could, for example, be contained in the identification or be determinable from the identification. Furthermore, the blind sample may be supplemented with an indicator which, for example, reacts irreversibly at the wavelength used for the measurement and renders the blind sample unusable for further measurements or produces a visible change in the blind sample.

Preferably, blind samples for testing UV/VIS spectrometers are in the form of a pre-filled, sealed cuvette holding a dissolved test substance which can be placed directly in the analytical instrument.

In a further embodiment, the analytical instrument is a density measuring instrument and/or a refractometer. The associated measurement value is then the density and/or the refractive index of the test substance.

As already mentioned, the method of the invention may be carried out for two or more blind samples wherein they may contain the same test substance and the same set values; the same test substance and different set values; different test substances and the same set values; or different test substances and different set values.

Furthermore, substances which are in the environment of the analytical instrument with generally known parameters, such as air, can be measured as a further blind sample and incorporated into the determination of the test result.

The test substance and the type of blind samples are selected as a function of the analytical instrument to be tested and/or the application to be tested. The term "application" as used here indicates an application which is specific to an analytical instrument which comprises a specific instrument configuration and/or selection of the measurement program.

In a further aspect, the invention concerns a system for testing the functional capability of an analytical instrument by means of the method of the invention. The system comprises an analytical instrument, a test unit, an output unit and at least one first and second blind sample. The analytical instrument again comprises at least one sensor, a control unit and a test program, wherein at least a first and second measurement value of the first and second blind sample is acquired using the analytical instrument. Each blind sample comprises a test substance and identification means with an unique identification for the respective test substance. The test unit comprises an acquisition module, a data processing module, a data module and a transfer module. Using the transfer module, data and information can be transferred between the control unit and the test unit. Using the acquisition module, the first and second identifications and the at least first and second measurement value from the first and second blind samples can be acquired and by means of the identification, a first and second set value for the first and second test substance of the respective blind sample can be determined, wherein the test substances and the set values are stored in the data module. Using the data processing module, a test result can be determined by comparing the at least first and second measurement value or at least a first and second test value correlated with this measurement value with the set values stored in the data module making use of a first and second threshold value stored in the data module, and after transferring the test result via the transfer module from the test unit to the control unit, can be output by means of the output unit.

As the analytical instrument, the system preferably comprises a titrator, a UV/VIS spectrometer, a refractometer, a pH meter, a conductivity measurement instrument, an instrument for determining density and/or an instrument for determining the ionic concentration or the quantity of a dissolved gas, in particular oxygen. Furthermore, the analytical instrument can be constructed such that it can acquire several parameters from a sample.

The output unit may, for example, be a display unit, such as a display or a monitor, a printer, a storage module and/or a means for optical and/or acoustic presentation. The result can, for example, be presented to the operator as an optical or acoustic signal, as a document or a symbol, stored in the analytical instrument and/or archived as a certificate, electronically or on paper.

The blind sample can further comprise a receptacle in which the test substance is present as a solid or in the dissolved form. The construction of the receptacle is matched to the analytical instrument to be tested so that preferably, the operator can measure the blind sample directly and/or without further sample preparation.

In addition, the blind sample may comprise an indicator which visually distinguishes a blind sample which has already been used in the test method.

BRIEF DESCRIPTION OF THE DRAWINGS

The method of the invention and various systems for carrying out the method will now be described in more detail with the aid of the accompanying drawings in which identical elements are given the same reference numerals and in which.

DETAILED DESCRIPTION

Figure 1:
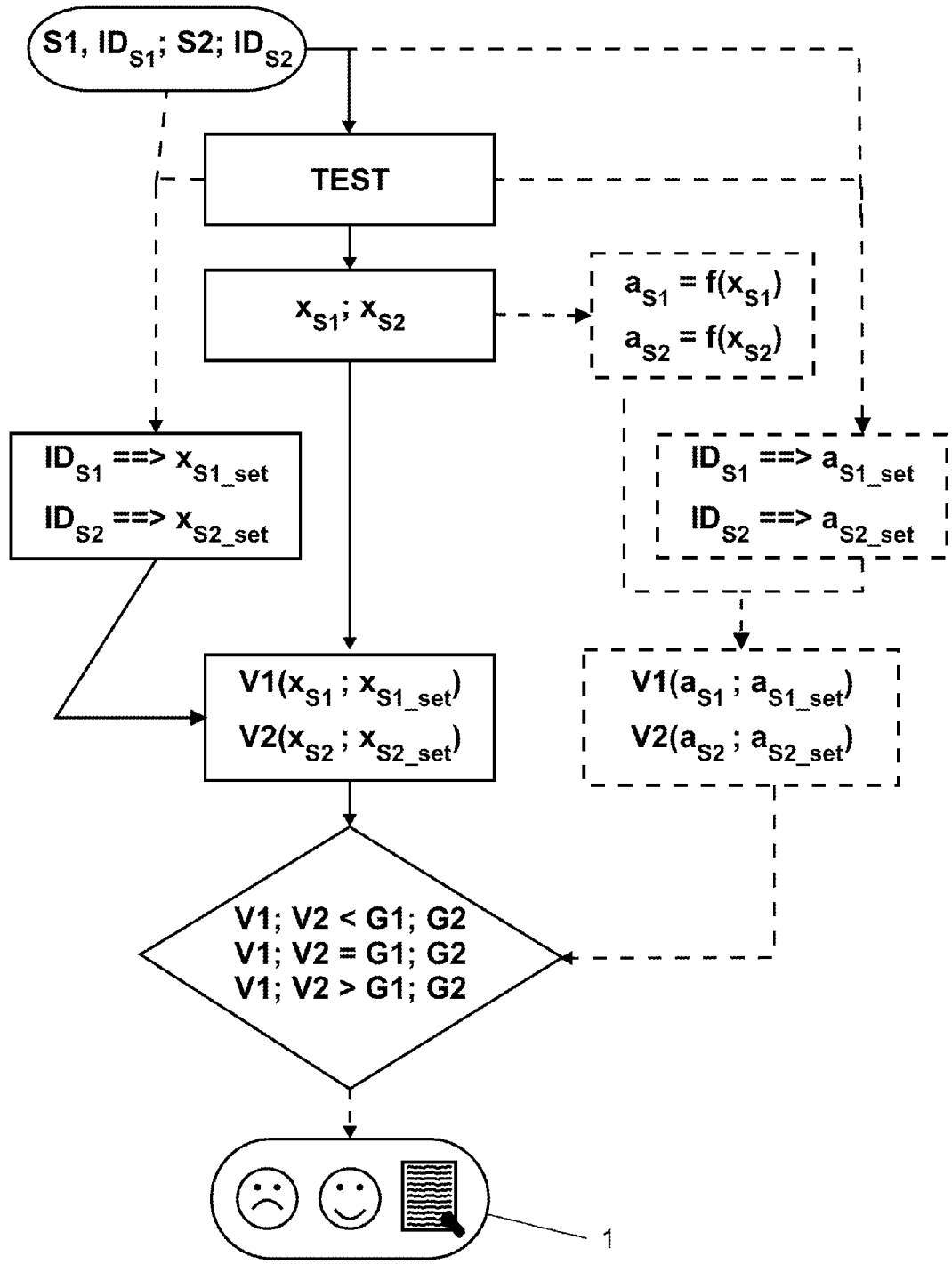
FIG. 1 is a schematic representation of the method of the invention for testing an analytical instrument.

FIG. 1 shows a schematic representation of the method of the invention for testing an analytical instrument.

The method comprises providing a first and second blind sample S1, S2, each of which comprises a test substance and an unique first and second identification $ID_{S1}$, $ID_{S2}$.

After selecting the suitable test program, firstly the instrument configuration is checked; this is denoted here as TEST. The instrument configuration can be checked directly based on the presets in the test program and/or using the selected first and second blind sample S1, S2, so that the instrument configuration is optimized for the test program and/or the blind samples S1, S2 employed. Next, the first and second blind samples S1, S2 are measured using the analytical instrument and a first and second measurement value $x_{S1}$, $x_{S2}$ is determined. Using the first and second identifications $ID_{S1}$, $ID_{S2}$, the test unit can be used to determine a first and second set value $x_{S1\_set}$, $x_{S2\_set}$, which is compared with the corresponding measurement value $x_{S1}$, $x_{S2}$. This comparison provides a first and second comparative value or a first and second comparative function, denoted here as $V1(x_{S1}; x_{S1\_set})$; $V2(x_{S2}; x_{S2\_set})$. Clearly, it is also possible that just one of the comparative functions or comparative values comprising a first and second comparative value or comparative function is determined. The comparison can be a simple difference and/or comprise known statistical evaluation routines, depending on the number and type of the measurement values. The comparison is carried out making use of a first and second threshold value or threshold value range G1, G2, which is a measure of the permitted deviation of the first and second measurement value $x_{S1}$, $x_{S2}$ from the respective set value $x_{S1\_set}$, $x_{S2\_set}$. The test result 1 is determined and presented using the deviation from the first and second threshold value G1, G2. If the first and second set value $x_{S1\_set}$, $x_{S2\_set}$ deviate from the first and second threshold values G1, G2, an error message is output as the test result 1, which may contain indications of the possible cause of the error and/or possible remedies. Furthermore, the test result 1 can be shown as a simple confirmation, or when at least three blind samples have been measured, as an independent or validated confirmation.

Instead of the measurement values $x_{S1}$, $x_{S2}$, the test result 1 may also be determined using a first and second test value $a_{S1}$, $a_{S2}$ and an associated first and second test set value $a_{S1\_set}$, $a_{S2\_set}$, wherein the test values $a_{S1}$, $a_{S2}$ are correlated with the respective measurement value $x_{S1}$, $x_{S2}$ and $a_{S1}=f(x_{S1})$ or $a_{S2}=f(x_{S2})$. The first and second test values $a_{S1}$, $a_{S2}$ may, for example, be a value determined from the respective measurement value $x_{S1}$, $x_{S2}$.

The method of the invention may also be carried out with three or more blind samples. The measurement values from all of the blind samples are included in the comparison and thus in the determination of the test result.

Figure 2:
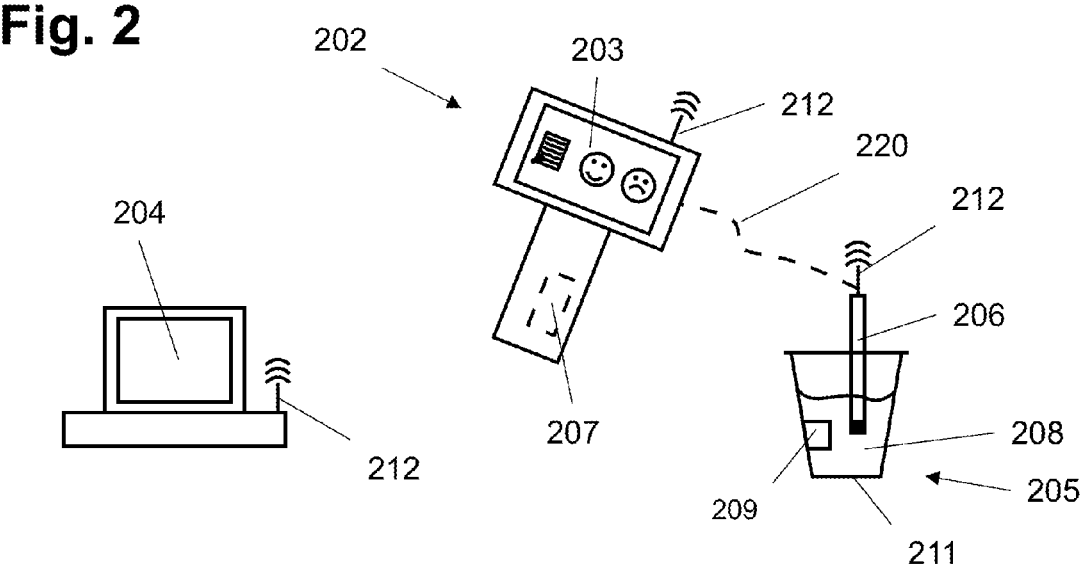
FIG. 2 is a schematic representation of an analytical instrument.

FIG. 2 shows, in a highly schematic form, a system for carrying out the method of the invention with an analytical instrument 202 which comprises a control unit 207, a sensor 206 and an output unit 203. The output unit 203 in this case is constructed as a display unit or display integrated into the analytical instrument 202. In the embodiment shown, the output unit 203 and the control unit 207 are linked together or are in the same casing. The sensor 206 can be connected to the control unit 207 either via the cable 220 shown here or via suitable transmission means 212. The transmission means 212 may, for example, be a wireless transceiver unit or internet data transfer or web-based data transfer. In order to test the analytical instrument 202, the sensor 206 is in contact with a test substance 208 of a blind sample 205. The blind sample further comprises a receptacle 211 in which the test substance 208 is placed and an unique identification means 209 with an identification for determining the type and one or more parameters of the test substance 208. Furthermore, the system comprises a test unit 204, which in this embodiment further comprises a transmission means 212 for communication with the control unit 207. The test unit 204 and the output unit 203 can, for example, be constructed as a web-based application and display unit so that the test result is determined by the web-based application and output to the operator via a suitable display unit such as a screen or display. The system shown in FIG. 2 may be constituted, as the analytical instrument 202, for example, by a pH meter, a conductivity measurement instrument, an instrument for determining redox potential, for ionic determination and/or for determining the concentration of dissolved gases, in particular oxygen. The analytical instrument 202 can be constructed as what is known as a bench-top instrument or as a hand-held instrument.

Figure 3:
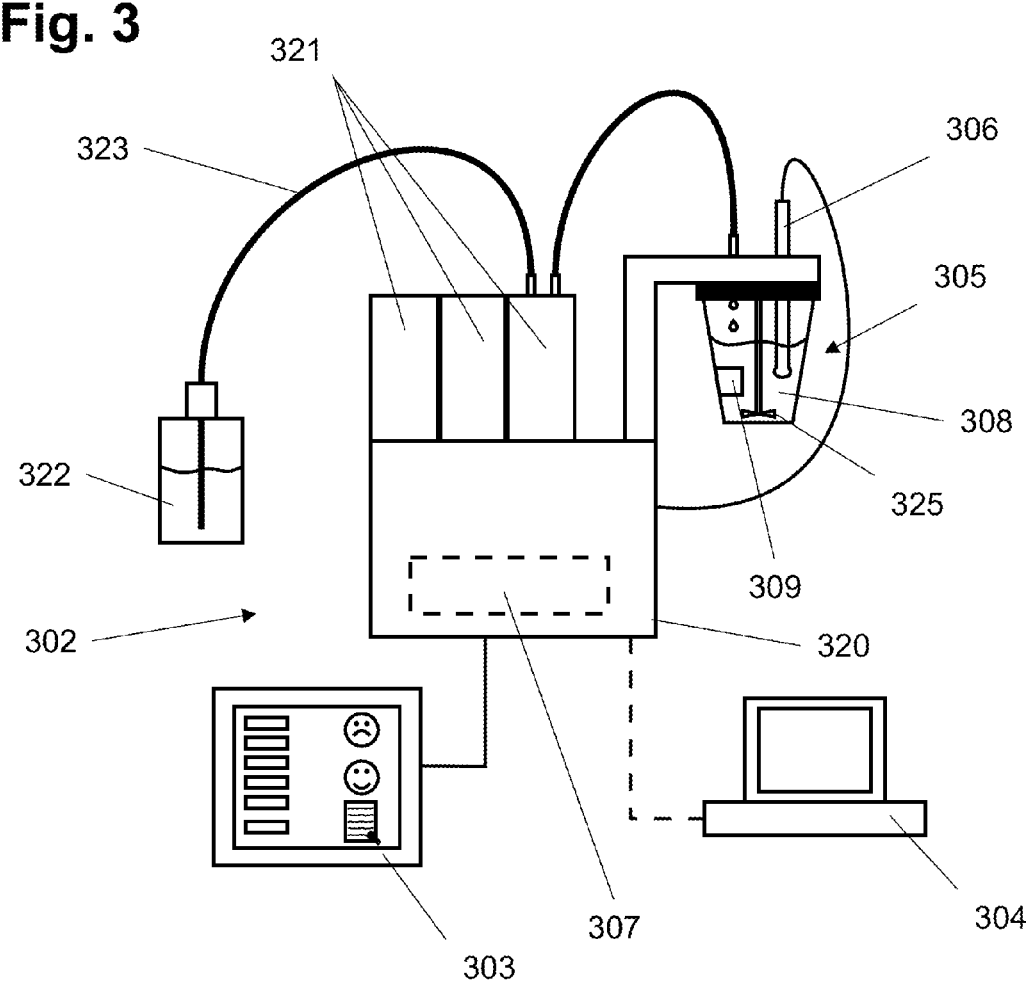
FIG. 3 is a schematic representation of a titrator as the analytical instrument.

FIG. 3 shows, in a highly schematic manner, a system for testing the functional capability of a titrator 302 as the analytical instrument. The system comprises the titrator 302, an output unit 303, a test unit 304 and a blind sample 305.

The titrator 302 comprises a housing 320 in which a control unit 307, shown here only in outline, is arranged. Further, the titrator 302 comprises at least one dosing element 321—three are shown here—with which a titration solution 322 can be dispensed into the blind sample 305. Each dosing element 321 is designed to dose one titration solution. A plurality of dosing elements 321 mean, for example, that the titrator 302 can be used for titrating different substances or to provide titration solutions with different titres. The dosing element 321 in this case is connected via fluid connections 323 on the one hand to one of the storage tanks containing the titration solution 322 and on the other hand to the blind sample 305 via a support 324. The support 324 is fastened to the housing 320 in this case.

Figure 4:
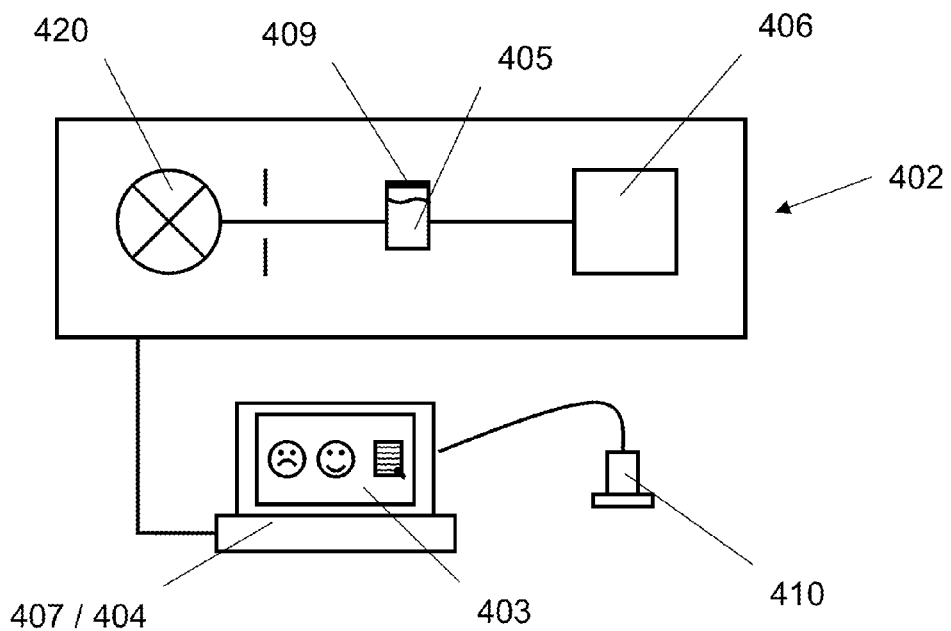
FIG. 4 is a schematic representation of a UV/VIS spectrometer as the analytical instrument.

The blind sample 305 comprises a receptacle in which are placed a solution of a test substance 308 and an unique identification means 309 fixed onto the receptacle. The identification means 309 may, for example, be a RFID tag, a serial number, a barcode or a matrix code. A reader to read off the identification of the identification means 309 can, as shown in FIG. 4, be connected to the analytical instrument or integrated therein. Thus, the identification can be acquired by the operator and manually input, in particular when it is a serial number.

During operation of the titrator 302, a stirrer 325 to mix up the sample during titration and at least one sensor 306 are arranged in the test substance solution 308. For acid-base titration, a pH sensor may be employed, for example.

The output unit 303 is linked to the titrator 302 via a cable. The test unit 304, which is shown here as a computer, can be linked to the control unit 307 directly or via a suitable data transfer link. The data transfer may be carried out via a cable, a wireless link, via the Ethernet or another device suitable for data transfer, as indicated by the broken line connecting the titrator 302 and the test unit 304.

The method for testing the functional capability of a titrator will be described below using an acid-base titration as an example. The operator is supplied with at least two blind samples comprising a test substance and identification means. Each blind sample comprises a receptacle with a cover, containing the dissolved test substance. The first blind sample contains, for example, tris(hydroxymethyl)-aminomethane (TRIS) as the test substance in a first amount dissolved in water. The second blind sample contains the same test substance or another test substance in a second amount as an aqueous solution. The amount is not known to the operator, but can be determined by the test unit from the unique identification, as can also the absolute weighing error. Together with the blind samples, the operator is given instructions regarding the instrument configuration and the titration solution and its titre to be used. For an acid-base titration, for example, 0.1 N sodium hydroxide is required, which the operator provides and which is connected to the dosing unit of the titrator.

To carry out the measurement, the operator removes the cover from the receptacle, preferably in a manner such that no substance residues are left on the cover, places the blind sample in the titrator and selects the test program.

By means of the identification of the first and/or second blind sample, the operator obtains information regarding manual testing or the analytical instrument obtains information regarding automatic testing of the instrument configuration. In this manner, in particular, a test is carried out as to whether the correct sensor and the correct titration solution is being used. After successfully testing the instrument configuration, the first blind sample it titrated and the first measurement value is acquired. Then the second measurement value of the second blind sample is acquired. If the operator wishes to obtain an independent or validated confirmation, at least a third and/or further blind sample is measured.

The first and second measurement value, the titre of the titration solution and the first and second identification are then transmitted to the test unit and processed further therein. This can be carried out by inputting the data to a web page or by automatic transfer of the data to the external or internal test unit. These data are used to request a first and second set value from the test unit for the respective blind sample and a comparative value or a comparative function is formed with the respective measurement value. In order to determine the test result, the comparative function or the comparative value is compared with a first or second threshold value. Each threshold value constitutes a measure of the allowed deviation of the respective measurement value from the set value.

The test result is determined by the test unit and transferred to the control unit which outputs it to the operator on the output unit. If the measurement values deviate too much from the set values, then an error message or error analysis is displayed. If the measurement values are within the error tolerance set by the threshold value, then the operator is presented with a simple confirmation when measuring two blind samples and an independent or a validated confirmation when measuring three or more blind samples.

FIG. 4 shows, in highly schematic manner, a system for testing the functional capability of a UV/VIS spectrometer 402 as the analytical instrument with a connected control unit 407 which comprises a test unit 404 and an output unit 403.

The spectrometer 402 comprises a light source 420 which is a broad spectrum light source, such as for example a laser or a laser diode, and a detector as the sensor 406. The radiation emitted by the light source 420 is guided through a blind sample 405 and, following interaction with a test substance contained in the blind sample 405, is detected by the detector 406. Depending on the bandwidth of the light source 420, the measurement result might be determined as a spectrum, i.e. the absorption or transmission distribution with respect to the wavelength or wave number, or as individual absorption or transmission values at a specific wavelength or wave number.

The blind sample 405 for a spectrometer is preferably a solution of the test substance in a cuvette which is optically transparent to the radiation used. The blind sample 405 additionally comprises identification means 409 which are attached outside the light path, for example and as shown here, at the top of the blind sample 405

A reader 410 can be connected to the control unit 407, with which the identification of the identification means is acquired and can be transferred to the control unit 407.

In order to carry out the method of the invention with a UV/VIS spectrometer, at least two blind samples, preferably with different test substances and/or different parameters are provided. Each blind sample is preferably supplied as a clear solution in a suitable and sealed cuvette with an identification means which can be used directly by the operator. In contrast to titration, in UV/VIS spectroscopy, the sample is not consumed and can be used several times. In order to prevent old blind samples from being used for testing, the solution of the test substance can be supplemented with an indicator which, for example, experiences a change under the influence of the radiation used for the measurement which results in a visible change in the blind sample, for example a colour change. Equally, the identification means may contain a "best before" date in the identification which is acquired by the test unit and which prevents old samples from being measured. In addition, testing of the instrument configuration of the spectrometer can comprise a calibration with air or without the cuvette or sample which is routinely and often carried out. A spectrum, at least one absorption value or at least one intensity for each blind sample is acquired as the measurement value. Evaluation of the measuring results and determination of the test result are essentially carried out as already described, whereby either the measurement values directly or the test value determined from the measurement values can have an influence on the result. If the absorption is measured as the measurement value then, for example, the transmission can be calculated from it and used as the test value.

Figure 5:
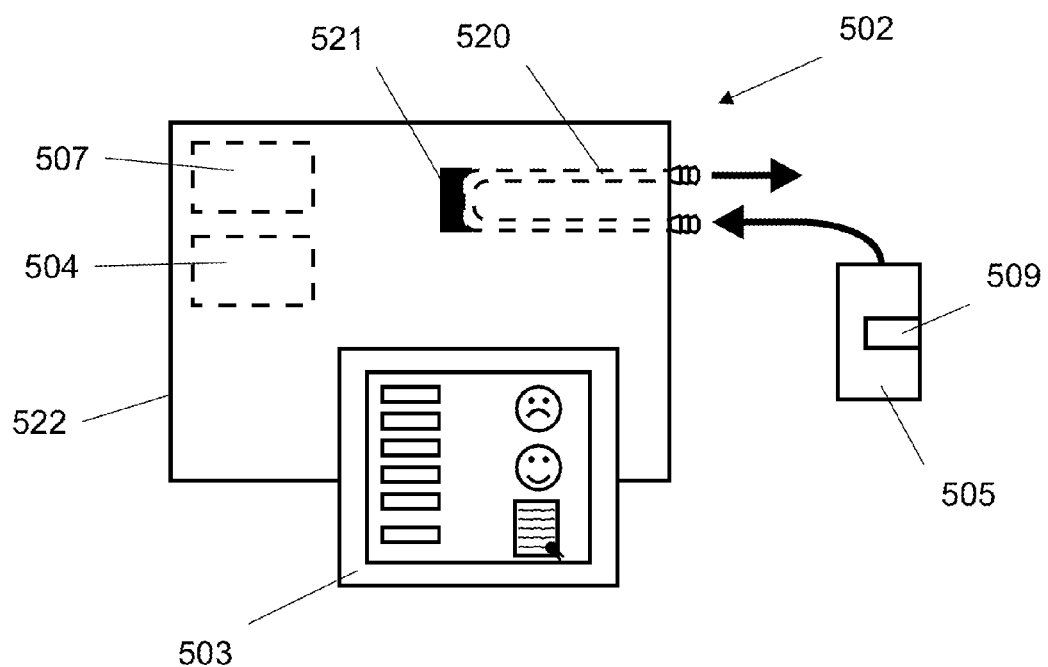
FIG. 5 is a schematic representation of an analytical instrument for determining density as the analytical instrument.

FIG. 5 shows, in highly schematic manner, a system for testing the functional capability of a density measuring instrument 502 as the analytical instrument.

In order to determine density with the density measuring instrument 502 shown in FIG. 5, a fluid blind sample 505 is introduced into an oscillatable U-shaped measuring cell 520, for example a glass tube. The fluid-filled measuring cell 520 is then excited so that it undergoes undamped vibration or oscillation by means of an oscillation unit 521. The density of the blind sample 505 can be determined using the change in the frequency and period of the oscillation compared to a measuring cell 520 filled with a standard sample. The density measuring instrument shown here is also termed a flexural resonator.

The measuring cell 520 is arranged in a housing 522 of the density measuring instrument along with a control unit 507 and a test unit 504. Further, the density measuring instrument comprises an output unit 503.

In addition, the blind sample 505 has identification means 509 with an unique machine-readable identification. The blind sample 505 can, for example, be injected into the measuring cell 520 or it can also be sucked in with a pump. To determine the density, the measuring cell should be full and as free from bubbles as possible.

To test a density measuring instrument using the method of the invention, the test substance of the respective blind sample is transferred from the receptacle into the measuring cell of the density measuring instrument and measured there. Preferably, the identification of the identification means is read prior to the respective measurement and then transmitted directly from the control unit to the test unit, thereby largely excluding transmission errors. The density of the first and second blind sample is acquired as the first and second measurement value; the test substances are preferably in a form which is capable of flowing.

Figure 6:
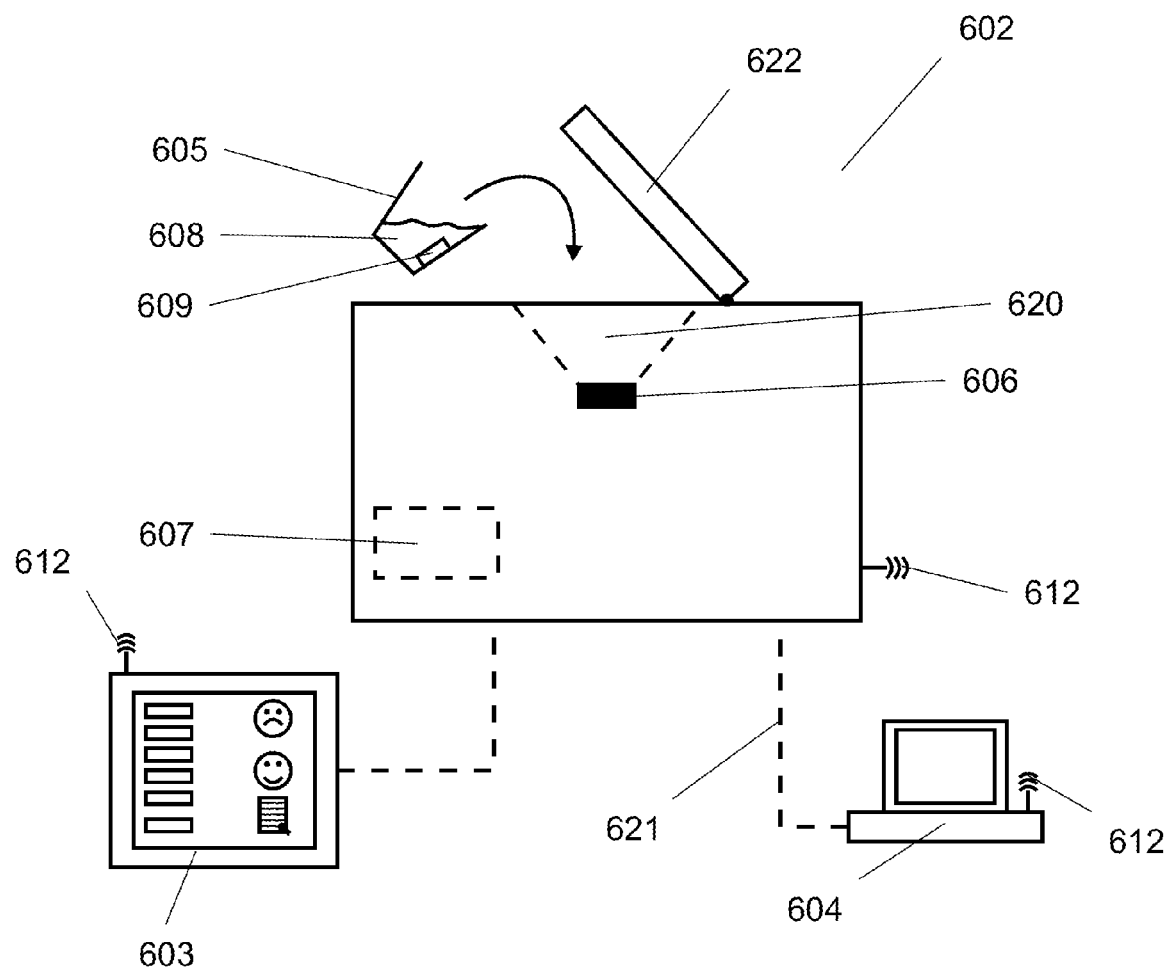
FIG. 6 is a schematic representation of a refractometer as the analytical instrument.

FIG. 6 shows, in highly schematic manner, a system for testing the functional capability of a refractometer 602 as the analytical instrument.

A refractometer 602 can be used to determine the refractive index of a blind sample 605 which is arranged in a measuring cell 620 and which is screened from incident light from outside by means of a cover 622. An optical unit 606 is arranged at the bottom of the measuring cell 620 and used to determine the refractive index by reflection. The blind sample 605 is supplied to the operator as a receptacle with identification means 609 in which a test substance 608 is placed. The refractometer 602 further comprises a control unit 607.

The system further comprises an output unit 603 and a test unit 604. The output unit 603 and/or the test unit 604 can either be connected directly to the control unit 607 via a suitable communication cable 621 or as an external unit via suitable communication means 612. The term "communication means" 612 as used here should be understood to mean both direct radio links, connections via a WLAN and/or another type of web-based link.

As was the case with the density measuring instrument, when testing the refractometer using the method of the invention, the test substance in the blind sample, which is preferably flowable, is transferred from the receptacle to the measuring cell of the refractometer and the refractive index of the test substance is determined at least once, preferably several times as the measurement value.

Instead of the individual receptacle shown here, an analytical instrument can also cooperate with a sample changer or sample carousel, not shown, which comprises a plurality of samples which are automatically measured one after the other. During series of tests, for example, after a given number of samples, at least two blind samples can be arranged in the sample changer the identification of which is automatically acquired from a reader arranged in the sample changer, whereupon the test program automatically starts. In this manner, the functional capability of the analytical instrument during a series of measurements can readily be tested. The automatic selection and automatic start of the test program can clearly not only be triggered with a sample changer, but also by the control unit inputting the identification of any first and second blind sample.

Although the invention has been described by illustrating specific embodiments, clearly, many further embodiments and variations can be derived from a knowledge of the present invention; as an example, where the features of the individual embodiments are combined together and/or individual functional units of the embodiments are exchanged. In particular, parts of the system could be connected together by cables or wirelessly; in addition, the system could have a reader which is external to or internal to the analytical instrument. In addition, the test unit of the analytical instrument could be provided as an external unit, as an internal unit or as a subunit of the control unit having regard to the analytical instrument.

What is claimed is:

1. A method for testing a capability of an analytical instrument to perform a predetermined analytical function, the analytical instrument comprising at least one sensor, a control unit and an output unit, the method comprising the steps of:

activating a test program configured in the analytical instrument;

selecting a first and a second blind sample, each blind sample comprising a test substance of a composition unknown to a user, with each blind sample having an identification means associated therewith that provides a unique identification to the respective blind sample;

using the test program to determine whether a selected one of the at least one sensors, the control unit and output unit are configured for performing the predetermined analytical function;

acquiring at least one first measurement value by using the selected sensor to measure the first blind sample;

acquiring at least one second measurement value by using the selected sensor to measure the second blind sample;

transferring, to a test unit, the respective measurement values and the associated unique identifications for the first and second blind samples;

associating, in a database of the test unit, the unique identifications of each blind sample with a set value and a threshold value that is stored therein for the blind sample, the set value representing an expected measurement value for the blind sample and the threshold value representing a permitted deviation from the set value;

determining, in the test unit, a test result for each blind sample, by comparing the measurement value to the stored set and threshold values for the blind sample;

transferring the test result to the output unit; and outputting the test result by means of the output unit.

2. The method of claim 1, wherein:
the outputted test result is at least one of: an error message; a simple confirmation; an independent confirmation; or a validated confirmation of the functional capability of the analytical instrument.

3. The method of claim 2, wherein:
each unique identification provided by the identifying means comprises a machine-readable code that is acquired and transferred to the test unit.

4. The method of claim 3, wherein:
the test unit is arranged as a subunit of the control unit.

5. The method of claim 3, wherein:
the test unit is external to, and independent of, the analytical instrument.

6. The method of claim 1, wherein:
the test unit comprises a database that is configured for associating each of the unique identifications with at least one of: the corresponding set value and the corresponding test substance.

7. The method of claim 1, wherein:
the analytical instrument is a titrator comprising at least one sensor, at least one dosing element, at least one titration solution, having a known titre, that is dispensed by the dosing element, and a control unit in which the test program is stored;

each of the first and second blind samples comprises a test substance, provided in the form of a solution, and each blind sample has an identification means with a unique identification of the respective test substance;

the step of acquiring the first and second measurement values is achieved by titrating each of the first and second blind samples against the titration solution and correlating an amount of the titration solution consumed thereby for the respective titrations;

the step of transferring the respective measurement values and the associated unique identifications to the test unit is achieved by acquiring and transferring each of the unique identifications, the titre and the measurement values to the test unit, where the test result is determined.

8. The method of claim 1, wherein:
the analytical instrument is a UV/VIS spectrometer comprising a sensor, a radiation source and a control unit in which the test program is stored;

each of the first and second blind samples comprises a test substance in the form of a solution, and each blind sample is associated with an identification means with the unique identification of the test substance;

the step of acquiring the first and second measurement values is achieved by determining at least one of: a first and second absorption value and a first and second intensity of the first and second absorption value; and the step of transferring the respective measurement results and the associated unique identifications to the test unit is achieved by acquiring and transferring the unique identifications and the measurement values to the test unit.

9. The method of claim 1, wherein:
the analytical instrument is a density measuring instrument and the respective densities of the first and second blind samples are acquired as the at least one first and second measurement values.

10. The method of claim 1, wherein:
the analytical instrument is a refractometer and the respective refractive indexes of the first and second blind samples are acquired as the at least one first and second measurement values.

11. The method of claim 1, wherein:
the first and second blind samples comprise the same test substance and, between the respective blind samples, a value of a parameter being tested is either the same or is different.

12. The method of claim 1, wherein:
the first and second blind samples comprise different test substances and, between the respective blind samples, a value of a parameter being tested is either the same or is different.

13. A system for testing the functional capability of an analytical instrument having at least one sensor, a test unit, a control unit and an output unit, using the method as claimed in claim 1, the system comprising:
at least a first and second blind sample, each of the blind samples comprising a test substance of a composition unknown to the user, with each blind sample associated with an identification means for unique identification of the blind sample; and a test program, operatively configured as software on the analytical instrument and comprising:
an acquisition module, by way of which the unique identification and a first and second measurement value, obtained by the sensor from the first and second blind sample, are acquired;

a data module, by way of which the first and second blind samples and a first and second set value of the first and second blind sample are determined, using the unique identifications stored in the data module, the set value representing an expected measurement value for the blind sample;

a data processing module, by way of which a test result is determined, by comparing the first and second measurement value or at least one first and second test value correlated with the first and second measurement value with a first and second set value, making use of a first and second threshold value stored in the data module, each threshold value representing a permitted deviation from the set value; and a transfer module, by way of which data and information are transferred between the control unit and the test unit and by way of which the test result is sent to the output unit.

14. The system of claim 13, wherein:

the analytical instrument is selected from the group consisting of: a titrator, a UV/VIS spectrometer, a refractometer and a densitometer.

15. The system of claim 13, wherein:

each blind sample further comprises a receptacle in which the test substance is arranged as a solid or in a dissolved form.

16. The system of claim 13, wherein:

each blind sample comprises an indicator that visibly distinguishes whether the blind sample has already been used for the test method.

* * * * *